(12) United States Patent
Anderson et al.

(10) Patent No.: US 6,451,793 B1
(45) Date of Patent: Sep. 17, 2002

(54) SYNERGISTIC INSECTICIDAL FORMULATIONS OF PYRIDABEN AND STROBILURINS

(75) Inventors: Thomas E. Anderson, Cary; Hendrik L. Ypema, Apex; William M. Fletcher, Bahama, all of NC (US); Vivienne E. Harris, Canandaigua, NY (US)

(73) Assignee: BASF Corporation, Mt. Olive, NJ (US)

( * ) Notice: Subject to any disclaimer, the term of this patent is extended or adjusted under 35 U.S.C. 154(b) by 9 days.

(21) Appl. No.: 09/670,558

(22) Filed: Sep. 27, 2000

Related U.S. Application Data
(60) Provisional application No. 60/156,514, filed on Sep. 29, 1999.

(51) Int. Cl.$^7$ ........................ A01N 43/58; A01N 37/12; A01N 37/44
(52) U.S. Cl. ........................................ 514/247; 514/539
(58) Field of Search .................................. 514/247, 539

(56) References Cited

U.S. PATENT DOCUMENTS

| | | | |
|---|---|---|---|
| 4,104,376 A | 8/1978 | Zeck ........................... 424/216 |
| 4,613,617 A | 9/1986 | Sousa .......................... 514/521 |
| 4,686,256 A | 8/1987 | Boutni ......................... 524/318 |
| 4,709,078 A | 11/1987 | Schirmer et al. ............. 560/60 |
| 4,723,034 A | 2/1988 | Schirmer et al. ............. 560/60 |
| 4,767,773 A | 8/1988 | Ayad ........................... 514/351 |
| 4,877,787 A | 10/1989 | Taniguchi et al. ........... 514/247 |
| 4,914,128 A | 4/1990 | Schirmer et al. ............ 514/532 |
| RE33,989 E | 7/1992 | Wenderoth et al. .......... 514/522 |
| 5,187,184 A | 2/1993 | Lovell ......................... 514/406 |
| 5,491,168 A | 2/1996 | Kataoka et al. .............. 514/517 |

FOREIGN PATENT DOCUMENTS

| | | |
|---|---|---|
| DE | 37 33 220 A | 4/1989 |
| DE | 196 15 976 A | 10/1997 |
| EP | 0 393 641 A2 | 10/1990 |
| EP | 0 478 195 A1 | 4/1992 |
| EP | 0 738 716 A2 | 10/1996 |
| EP | 0 760 208 A2 | 3/1997 |
| JP | 8-198719 | 8/1996 |
| JP | H8-245311 | 9/1996 |
| JP | S63-303902 | 12/1998 |
| WO | WO 97/40676 | 11/1997 |

OTHER PUBLICATIONS

XP–002157487 (1996).
XP–002157484, 394–ICLA5504, Fungicide (1995).
XP–002157488 (1989).
XP–002157485 (1999).
CROPU Copyright 2001 Derwent Information Ltd (1996).

Primary Examiner—Allen J. Robinson
(74) Attorney, Agent, or Firm—Nixon & Vanderhye P.C.

(57) ABSTRACT

Insect infestation on growing plants is controlled by the administration of an insecticidally synergistically effective amount of a pyridazinone derivative and a fungicide to a locus of a growing plant in need of insect infestation control. Most preferably, the pyridazinone derivative is pyridaben and the fungicide is a strobilurin (e.g., kresoxim-methyl).

8 Claims, No Drawings

US 6,451,793 B1

SYNERGISTIC INSECTICIDAL FORMULATIONS OF PYRIDABEN AND STROBILURINS

DOMESTIC PRIORITY CLAIM

This application is related to, and claims domestic priority benefits under 35 USC §119(e) from, U.S. Provisional Patent Application Serial No. 60/156,514 filed on Sep. 29, 1999, the entire content of which is expressly incorporated hereinto by reference.

FIELD OF THE INVENTION

The present invention relates to compositions and methods for controlling insect pests on growing plants. In particularly preferred forms, the invention is embodied in compositions and methods for controlling pests using a synergistic insecticidal effective amount of a pyridazinone derivative (most preferably, pyridaben) and a fungicide (most preferably, a strobilurin).

BACKGROUND AND SUMMARY OF THE INVENTION

Synergism is the cooperative action encountered in combinations of two or more biologically active compounds in which the combined activity of the two compounds exceeds the sum of the activities of the compounds when used alone.

Specifically, U.S. Pat. No. 4,104,376 discloses a synergistic composition for insect control comprised of a combination of phosphoro dithioate and formamidine at a ratio of 1 to 0.1–1.0, preferably 1 to about 0.2–0.5. U.S. Pat. No. 4,613,617 discloses synergistic compositions for insect control comprising dione esters and other insecticides, such as pyrethroids, carbamates and organophosphates. U.S. Pat. No. 4,767,773 discloses synergistic compositions for insect control comprising benzoyl ureas and pyrethroids, carbamates, and organophosphates. U.S. Pat. No. 5,187,184 discloses that synergistic compositions for insect control comprising adding arylnitropyrrole or arylpyrrolecarbonitrile to a compositions of arylpyrazolecarboximide provides superior pest control at lower levels of the combined active ingredients than may be achieved with the arylnitropyrrole or arylpyrrolecarbonitrile or arylpyrrolecarbontrile applied alone at equal or higher levels than the total amount of active agent used in the combination treatment. U.S. Pat. No. 5,491,168 discloses synergistic compositions for insect control comprising propargite (tert butyl phenoxy cyclohexylpropynyl sulfite) and a pyrethroid. Finally, JP Kokai (A) H8-198719 published Aug. 6, 1996 discloses agricultural and horticultural fungicides comprised of a synergistic combination of a substance which inhibits the complex I enzyme reaction of the mitochondria electron transfer system (e.g., Pyridaben) and a substance which inhibits the complex III enzyme reaction of the mitochondria electron transfer system (e.g., kresoxim-methyl).

DETAILED DESCRIPTION OF THE INVENTION

The term "synergistically effective amount", as used herein, refers to the sub-lethal doses of two active ingredients blended together and administered conjointly which then provides a lethal pest killing effect of 80% or greater. In other words, "synergism" means the combined action of two or more agents blended together and administered conjointly that is greater than the sum of their individual effects.

"Sub-lethal dose range" as used herein refers to the dose range of a single agent at which the intended effect is only partially realized. The terms "effective lethal dose" or "lethal dose" as used herein refer to the dose range of a single agent at which the intended effect is realized to an extent of 80% or greater.

The insecticidal compositions of this invention will necessarily include an effective amount of a pyridazinone derivative. Preferably, the pyridazinone derivative will be one that is disclosed in U.S. Pat. No. 4,877,787 to Taniguchi et al (the entire content of which is expressly incorporated hereinto by reference). The most preferred pyridazinone derivative is tert-butylbenzylthio substituted chloropyridazin, specifically 2-tert-butyl-5-(4-tert-butylbenzylthio)-4-chloropyridazin-3(2H)-one colloquially known as Pyridaben.

The pyridazinone derivative will be present in the synergistic compositions of this invention in an amount between about 0.1 to about 99.9 wt. % (based on the total composition weight), more preferably between about 3 to about 97 wt. %, and most preferably between about 10 to about 90 wt. %.

Surprisingly, synergistic insecticidal activity has been discovered by the combination of a pyridazinone derivative described above and a fungicide. In other words, according to the present invention, greater insecticidal activity has been discovered if an effective amount of a fungicide was combined with the pyridazinone derivative described above as compared to the use of the pyridazinone derivative alone.

The referred fungicide is a strobilurin. As used herein and in the accompanying claims, the term "strobilurin" is meant to refer to natural and synthetic fungicides having strobilurin A as its lead molecule. Preferably, the strobilurins employed in the practice of the present invention are those described more fully in U.S. Pat. Nos. Re. 33,989 (Reissue of U.S. Pat. No. 4,829,085), U.S. Pat. No. 4,914,128, 4,686,256, 4,709,078 and 4,723,034, the entire content of each such prior-issues patent being incorporated hereinto expressly by reference. The most preferred strobilurin is methyl-(E)-2-methoxyimino-2-[2-o-tolyoxy-methyl)phenyl] acetate, commonly known as kresoxim-methyl.

The strobilurin derivative will be present in the synergistic compositions of this invention in an amount between about 0.1 to about 99.9 wt. % (based on the total composition weight), more preferably between about 3 to about 97 wt. %, and most preferably between about 10 to about 90 wt. %.

The compositions of this invention may be applied in the form of dusts, granules, solutions, emulsions, wettable powders, flowables and suspensions. Application of the composition is made according to conventional procedure to the locus of the plant in need of the same using the appropriate amount of the compound per acre as described below. According to the present invention the application of the composition to the "locus" of the plant includes application to the plant or parts of the plant or the soil in which the plant is growing.

The compositions are preferably applied to above ground portions of the plants. The application of liquid and particulate compositions to above ground portions of plants may be carried out by conventional methods, for example, boom and hand application, including sprayers or dusters. The compositions may be applied aerially as a spray, if desired. The compositions employed in the practice of the present invention are most preferably used in the form of aqueous solutions that may be applied in a conventional manner, for example, by spraying, atomizing or watering the locus of the plant.

The compositions of this invention may also be applied in conjunction with other ingredients or adjuvants commonly employed in the art. Examples of such ingredients include drift control agents, defoaming agents, preservatives, surfactants, fertilizers, phytotoxicants, herbicides, pesticides, insecticides, fungicides, wetting agents, adherents, nematocides, bactericides, trace elements, synergists, antidotes, mixtures thereof and other such adjuvants well known in the art.

The synergistic compositions of this invention may be applied to the above-ground portions of a plant in an insecticidally effective amount. Preferably, the compositions are applied in a single application in an amount between about 0.01 to about 5 pounds active ingredient per acre (lb ai/A), more preferably between about 0.01 to about 3 lb ai/A, and most preferably between about 0.1 to about 1.5 lb ai/A. Additional applications of these amounts may be required over the course of the growing season, depending on the presence of insect pests.

The present invention will be further understood from the following non-limiting Examples.

EXAMPLES

In the following Examples, the expected effect E was calculated using Limpel's formula E=X+Y−XY/100 (Richer, *Synergism—a Patent View*, Restic. Sci, vol. 19, pp. 309–315, 1987, the entire content of which is expressly incorporated hereinto by reference. Thus, if the observed effect is greater than the expected effect E, then synergism is said to be exhibited. If the observed effect is less than the expected effect E, then antagonism is said to be exhibited.

In the following Examples, the pyridaben compound was BAS 300 (Sanmite® insecticide, BASF Corporation) and the kresoxim methyl was BAS 490 (Cygnus® fungicide, BASF Corporation).

Example 1

A greenhouse trial was conducted to determine the insecticidal effects against the cotton aphid (*Aphis gossypii*). In this regard, cotton plants infected with the cotton aphid were sprayed in a growth chamber and placed in a greenhouse. Counts were made on apterous forms at 6 and 16 days after treatment (DAT), with the data appearing in Tables 1 A and 1 B below.

TABLE 1A

| | % Cotton Aphid Control 6 DAT | | | |
|---|---|---|---|---|
| | 5 ppm | 10 ppm | 50 ppm | 100 ppm |
| X; BAS 300 | 73.8 | 75.2 | 94.5 | 97.6 |
| Y; BAS 490 | 11 | 0 | 0 | 0 |
| X + Y (1:1 ratio) Observed | 68.6 | 98.6 | 99 | 99.7 |
| Expected | 84.8 | 75.2 | 94.5 | 97.6 |

TABLE 1B

| | % Cotton Aphid Control 16 DAT | | | |
|---|---|---|---|---|
| | 5 ppm | 10 ppm | 50 ppm | 100 ppm |
| X; BAS 300 | 68.9 | 70.4 | 98 | 99.1 |
| Y; BAS 490 | 13.3 | 14.3 | 4.4 | 26.6 |
| X + Y (1:1 ratio) Observed | 43.1 | 99.1 | 99.3 | 99.7 |
| Expected | 73 | 84.7 | 98.2 | 99.3 |

As can be seen, synergistic insecticidal effects against the cotton aphid was apparent at an application rate of 10 ppm active ingredient (ai).

Example 2

Example 1 was repeated except using celosia infected with green peach aphids (*Myzus persicae*) and using the application rates noted. The data appear in Table 2 below.

TABLE 2

| | % Green Peach Aphid Control | | | | |
|---|---|---|---|---|---|
| | 2 DAT | 4 DAT | 6 DAT | 10 DAT | 14 DAT |
| X; BAS 300 0.9 lb ai/100 gal | 0 | 47 | 77 | 97 | 95 |
| Y; BAS 490 0.1 lb ai/100 gal | 0 | 14 | 5 | 10 | 5 |
| X + Y (9:1 ratio) Observed | 20 | 99 | 99 | 100 | 100 |
| Expected | 0 | 54 | 78 | 97.3 | 95.25 |

Example 3

Example 1 was repeated except using dracaena infected with twospotted spider mites (*Tetranychus urticae*) and using the application rates noted. The data appear in Table 3 below.

TABLE 3

| | % Twospotted Spider Mite Control | |
|---|---|---|
| | 7 DAT | 14 DAT |
| X; BAS 300 2 oz formulated product/100 gal | 80 | 91 |
| Y; BAS 490 3.2 oz formulated product/100 gal | 16 | 28 |
| X + Y Observed | 92 | 96 |
| Expected | 83.2 | 93.5 |

Example 4

Example 1 was repeated and the number of apterous aphids (AA) per plant at 6 and 16 DAT were noted. The data appear in Table 4 below versus a conventional insecticide, imidacloprid (Provado® insecticide commercially available from Bayer Corp.).

TABLE 4

| | ppm ai | # of AA 6 DAT | # of AA 16 DAT |
|---|---|---|---|
| Untreated | | 290 | 750 |
| BAS 300 | 5 | 76 | 233 |
| | 10 | 72 | 222 |
| | 50 | 16 | 15 |

TABLE 4-continued

|  | ppm ai | # of AA 6 DAT | # of AA 16 DAT |
|---|---|---|---|
|  | 100 | 7 | 7 |
|  | 200 | 1 | 4 |
|  | 300 | 2 | 2 |
| BAS 490 | 5 | 258 | 650 |
|  | 10 | 290 | 643 |
|  | 50 | 298 | 717 |
|  | 100 | 316 | 550 |
| BAS 300 BAS 490 | 5 + 5 | 91 | 428 |
| BAS 300 BAS 490 | 10 + 10 | 4 | 7 |
| BAS 300 BAS 490 | 50 + 50 | 3 | 5 |
| BAS 300 BAS 490 | 100 + 100 | 1 | 2 |
| PROVADO | 100 | 0 | 3 |

The data above demonstrate the excellent intrinsic activity of BAS 300 against the cotton aphid; moderate activity at 6 DAT was observed at an application rate of 5ppm ai. Synergism was apparent with the combination of BAS 300 and BAS 490 at 10 ppm which was significantly superior to BAS 300 alone at 10 ppm. BAS 490 was ineffective alone at all rates against the cotton aphid. The combination of BAS 300 and BAS 300 and BAS 490 at 10 ppm was comparable in effectiveness against the cotton aphid as compared to the PROVADO® insecticide control.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of controlling insect infestation on growing plants comprising applying to a locus of a growing plant in need of insect infestation control an insecticidally synergistically effective amounts of a pyridabem and kresoxim-methyl.

2. The method of claim 1, wherein the pyridaben is present in an amount between about 0.1 to about 99.9 wt. %, based on the total composition weight.

3. The method of claim 2, wherein the pyridaben is present in an amount between about 3 to about 97 wt. %, based on the total composition weight.

4. The method of claim 2, wherein the pyridaben is present in an amount between about 10 to about 90 wt. %, based on the total composition weight.

5. The method of claims 3 or 4, wherein the kresoxim-methyl is present in an amount between about 0.1 to about 99.9 wt. %, based on the total composition weight.

6. The method of claim 5, wherein the kresoxim-methyl is present in an amount between about 3 to about 97 wt. %, based on the total composition weight.

7. The method of claim 5, wherein the kresoxim-methyl is present in an amount between about 10 to about 90 wt. %, based on the total composition weight.

8. A method of controlling insect infestation on growing plants comprising applying to a locus of a growing plant in need of insect infestation control an insecticidally effective amount of an insecticidal composition which comprises, based on total composition weight, an insecticidally synergistically effective amount of between about 0.1 to about 99.9 wt. % of pyridaben, and between about 0.1 to about 99.9 wt. % of kresoxim-methyl.

* * * * *